Figure 1:
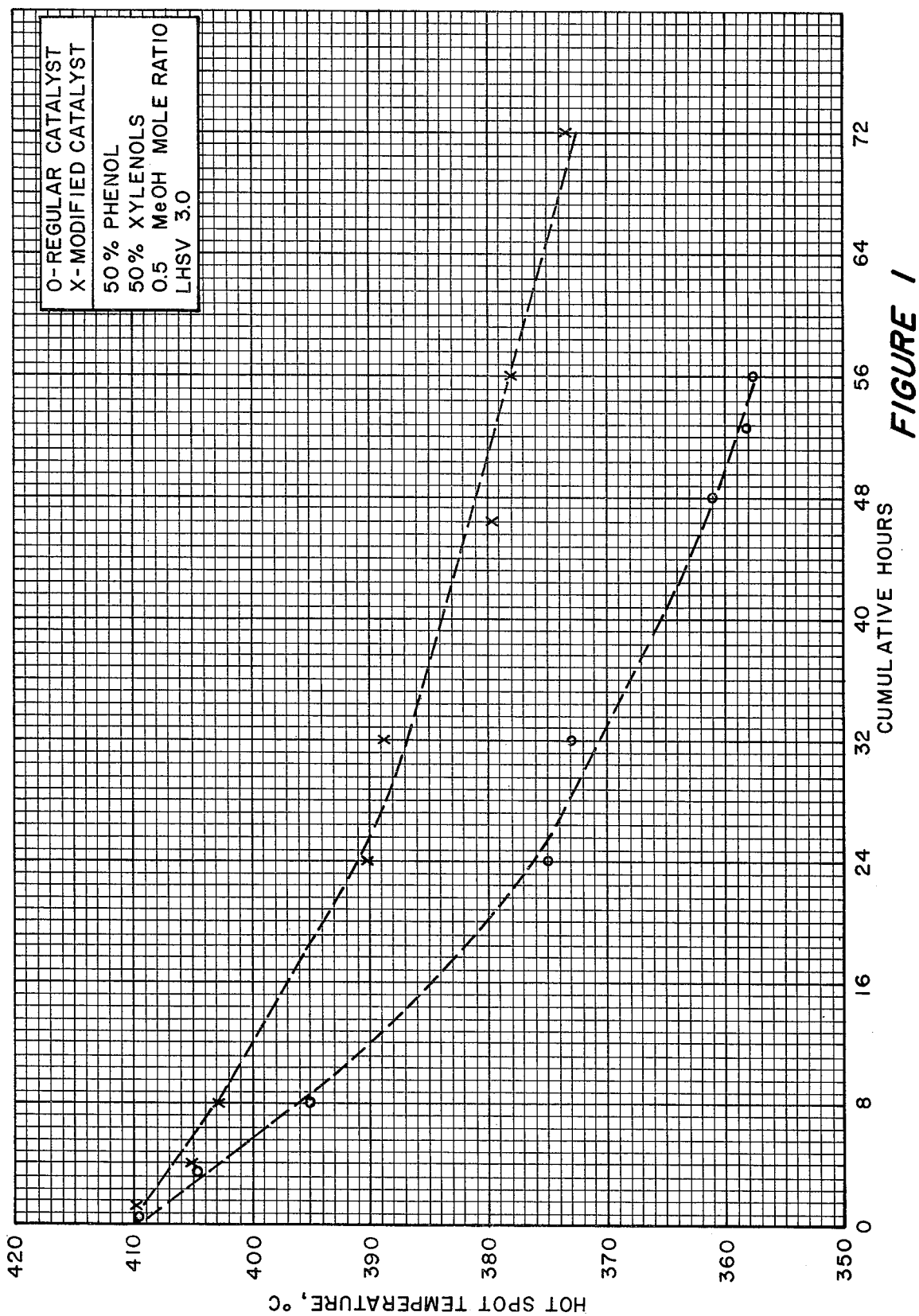

United States Patent [19]

Leach

[11] 4,126,749

[45] Nov. 21, 1978

[54] PHENOLICS METHYLATION USING A MODIFIED ALUMINA CATALYST

[75] Inventor: Bruce E. Leach, Ponca City, Okla.

[73] Assignee: Continental Oil Company, Ponca City, Okla.

[21] Appl. No.: 817,414

[22] Filed: Jul. 20, 1977

[51] Int. Cl.² .............................................. C07C 37/12
[52] U.S. Cl. .................................................... 568/804
[58] Field of Search ......................... 260/621 R, 624 C

[56] References Cited

U.S. PATENT DOCUMENTS

| | | | |
|---|---|---|---|
| 3,624,163 | 11/1971 | Del Bel et al. | 260/621 R |
| 3,737,466 | 6/1973 | Sharp et al. | 260/621 R |

Primary Examiner—James O. Thomas, Jr.
Assistant Examiner—Werren B. Lone
Attorney, Agent, or Firm—Cortlan R. Schupbach, Jr.

[57] ABSTRACT

Aluminas derived from aluminum alkoxide hydrolysis are calcined at 1150°–1800° F for a period of time ranging 0.5 to about 12 hours to develop specific pore volume and pore diameter characteristics prior to use as a catalyst in the vapor phase and liquid phase methylation of phenol, monosubstituted, and di-substituted phenols. The calcining at higher temperatures gives increased catalyst life, lower isomerization and disproportionation, and higher orthomethylation activity.

2 Claims, 3 Drawing Figures

EFFECT OF CALCINING TEMPERATURE ON CATAPAL® SB ALUMINA EXTRUDATE PORE SIZE DISTRIBUTION

EFFECT OF CALCINING TEMPERATURE ON CATAPAL® SB ALUMINA EXTRUDATE PORE SIZE DISTRIBUTION

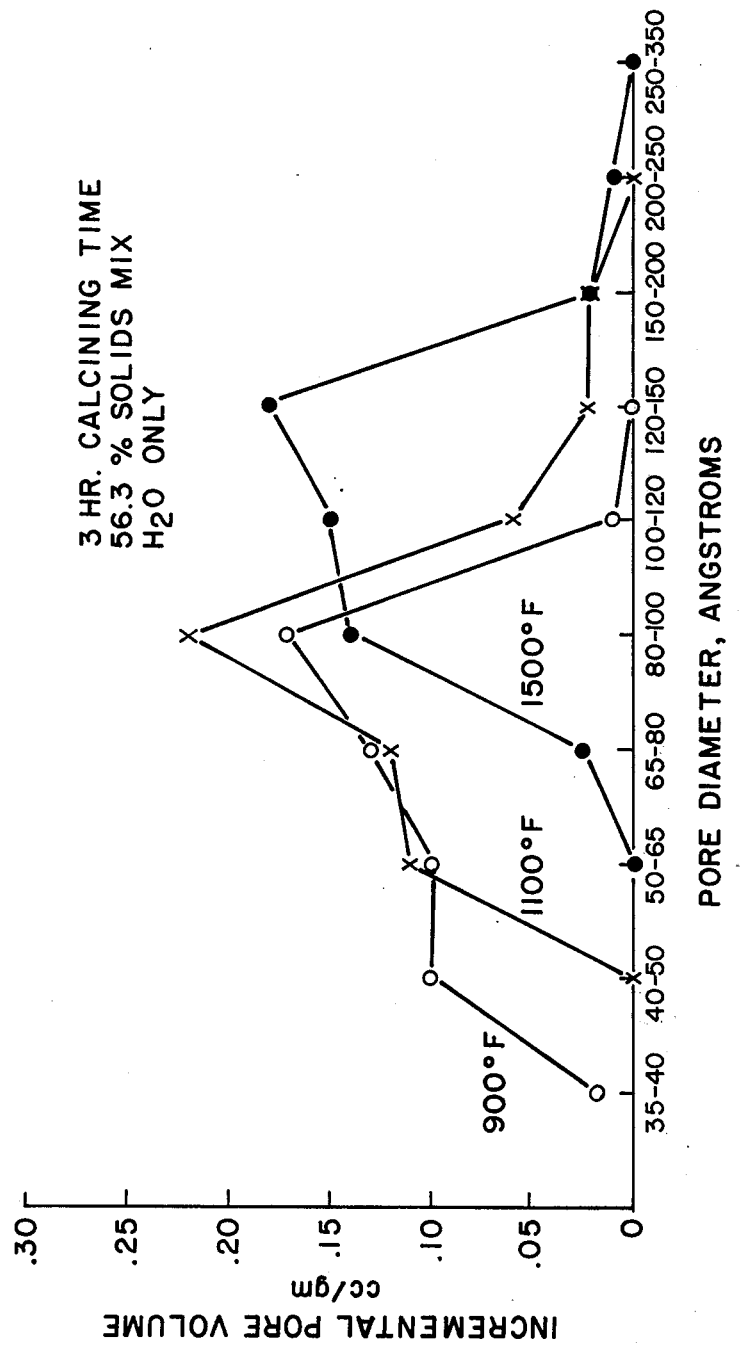

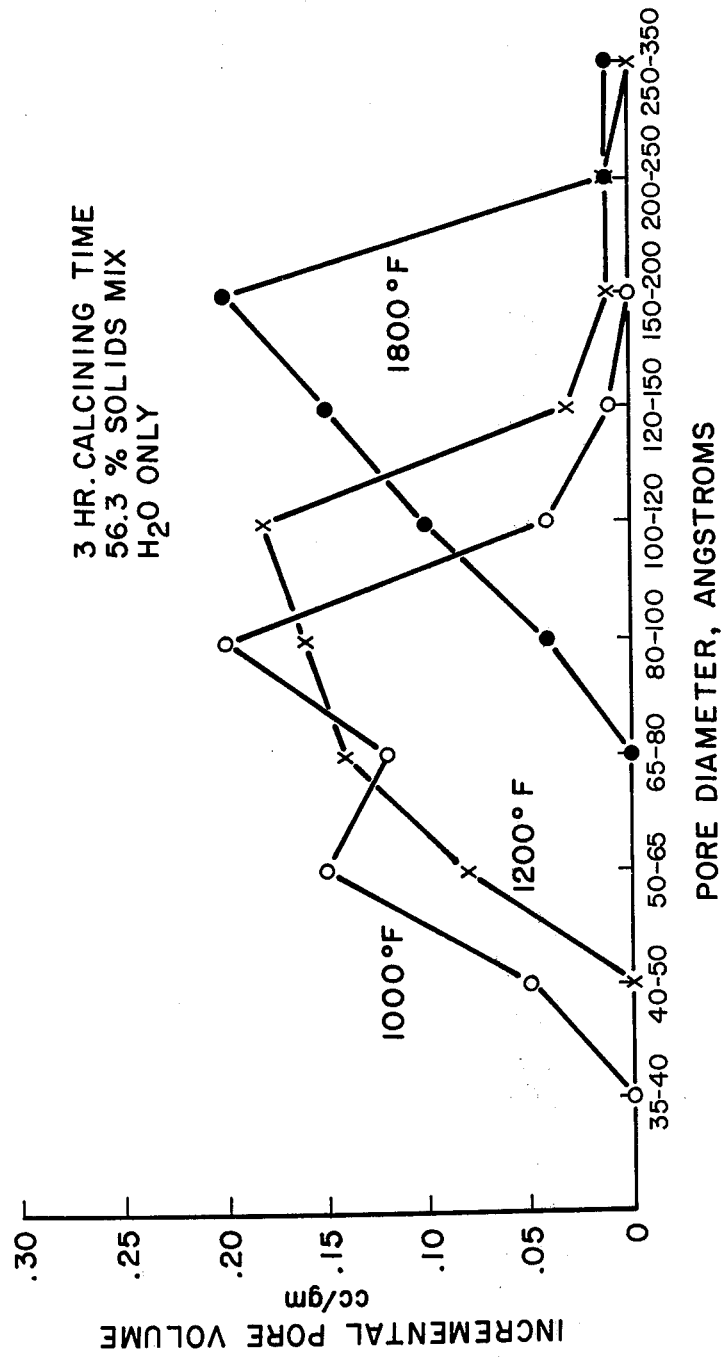

PHENOLICS METHYLATION USING A MODIFIED ALUMINA CATALYST

This invention relates to a modified alumina catalyst for use in methylation reactions. More particularly, this invention relates to a modified alumina catalyst having specific properties for use in phenol methylations in both the liquid and vapor phase.

Methylation reactions using alumina catalysts and especially alumina catalysts derived from the water hydrolysis of aluminum alkoxides, derived from the process known as the Ziegler method for making alcohols, are well-known in the art. This process can be found described in U.S. Pat. Nos. 4,022,843; 3,994,982; and 3,979,464 wherein liquid phase reactions are taught. However, the reactions described in these patents are carried out using alumina catalyst which are normally dried and calcined at temperatures of from about 900° F. to about 1100° F.

It has been believed in the prior art that in order for catalysts to have the most activity in reactions of methylating phenols, surface area was the primary criteria and that a high surface area is more desirable than a low surface area. Thus the catalyst used in these references was one having a surface area which allowed phenol methylation to occur in the liquid phase thus extending catalyst life and reducing formation of by-products over that of other aluminas, and especially when used in vapor phase methylations. However, selectivity to the desired products, while improved over alumina catalyst from other sources, still left something to be desired as by-product separation was expensive, troublesome, and non-productive. Thus it would be of great benefit to devise a process which would improve reaction rates and selectivity, especially in the vapor phase, while maintaining the benefits of liquid phase reactions, such as extended catalyst life, lower by-product production and improved selectivity.

It is therefore an object of the instant invention to provide a method for the methylation of phenols in the vapor and liquid phase having improved reaction rate and selectivity. Other objects will become apparent to those skilled in this art as the description proceeds.

It has now been discovered in accordance with the instant invention that methylation of phenols in the vapor phase can be increased in rate and improved in selectivity while greatly increasing catalyst life by using a modified alumina catalyst derived from the water hydrolysis of aluminum alkoxides. The modification is surprisingly simple, comprising calcining the alumina catalysts at temperatures higher than normal in the prior art. These calcinations take place at temperatures from 1150° F. to about 1800° F. for periods of time ranging from ½ to 10 hours.

Catalysts derived from hydrolysis of aluminum alkoxides have previously been calcined in this range. U.S. Pat. Nos. 4,012,313 and 3,852,190 show such calcinations. Other references which mention calcining such aluminas in this temperture range are found in U.S. Pat. Nos. 2,905,632; 2,859,185; 2,713,037; 2,796,326; 2,798,050; and 2,903,418. However these patents all teach that such calcining temperatures provide a catalyst which is useful only for reforming, ususally in combination with a metal or acting as a support for a metal such as platinum. These patents contain no suggestion that such a catalyst calcined at such conditions would be useful for the vapor or liquid phase methylation of phenols.

Thus it can be seen that phenolics methylation in the vapor phase using alumina catalyst derived from the water hydrolysis of aluminum alkoxides is well-known in the art. These aluminas have been found to have high activity for the reaction. These catalysts, however, require regeneration at periodic times in order to remove carbonization products on the catalyst which tend to decrease reaction time and selectivity.

The process of the instant invention solves these problems by increasing selectivity to materials such as orthocresol, 2,6-xylenol, and 2,3,6-trimethylphenol in the vapor phase phenol methylation. In addition, the catalyst of the instant invention allows a longer cycle time between catalyst regenerations by reducing carbonization on the catalyst. Thus the instant invention alleviates many of the major objections to the use of vapor phase.

The invention can be stated as a process for the liquid or vapor phase methylation of phenol, monosubstituted and di-substituted phenols to produce 2,6-xylenol, orthocresol, and 2,3,6-trimethylphenol in the presence of a gamma alumina catalyst at a pressure of from about 400 pounds per square inch gauge to about 1500 pounds per square inch gauge when the reaction is carried out in liquid phase, and 0.1 to 100 psig when the reaction is carried out in vapor phase, wherein (a) the gamma alumina is derived from aluminum alkoxide hydrolysis; (b) methanol/phenol mole ratios of from about 0.1 to about 3.0 are used, preferably 0.3 to 1.0; (c) while at a temperature of from about 300° C. to about 450° C., the improvement comprising calcining the gamma alumina catalyst at a temperature of from about 1150° F. to about 1800° F. for a period of time ranging from about 0.5 to about 12 hours prior to use in the reaction.

The additional heating of the alumina changes the amount of pores within angstrom ranges of about 65A° to about 200A°. The alumina catalyst of the instant process should have at least 50% of the pores larger than 65A° and at least 50% of the pores smaller than 200A°. Preferably, 70 to 80% of the catalyst pores will be in the range of about 80A° to about 150A°.

The process of the present invention can be carried out efficiently in a batch reactor or a continuous flow reactor. Of these the continuous flow reactor is preferred. In the continuous flow reactor the alumina catalyst is suitably divided and placed in a position to catalyze the reaction between the phenol and the methylating agent. The reactor flow can be either upward or by gravity; however, gravity flow is preferred.

When comparative runs are carried out under the same reaction conditions, the catalyst of the instant invention produces significantly higher yields and selectivities. One product, 2,3,6-trimethylphenol, while in minor proportions, is an extremely useful product for Vitamin E synthesis and can be recovered using conventional methods such as fractional distillation and/or recrystallization. Heavier materials produced can be removed by fractional distillation.

Major preferred products such as ortho cresol can be recovered at high yields as can 2,6-xylenol. The catalyst of the present invention, while exceptionally effective, produces some amounts of by-products, although these amounts are less than with a catalyst calcined at a lower temperature. The reduced amount of by-products thus allows the use of smaller amounts of recycle and recovery equipment, and also allows much longer catalyst life. By-products which are especially undesirable such as meta/para-cresol are produced in lower by-product/product ratios.

When the process of the instant invention is carried out in a continuous fashion a liquid hourly space velocity (LHSV) of from about 2–10 is preferred. In addition, pressures of from about 450 pounds per square inch gauge (psig) to about 800 pounds per square inch gauge (psig) and a methanol/phenol mole ratio of from about 0.2 to about 1.0 is preferred for liquid phase reactions. Throughout this specification, tables and claims, the following abbreviations are used:

DME — dimethylether
MeOH — methanol
DMA — dimethylanisole
TMP — trimethylphenol
TeMP — tetramethylphenol
PMB — pentamethylbenzene
PMP — pentamethylphenol The catalyst used for the purpose of these examples was CATAPAL SB alumina tablets, trademark of and sold by Continental Oil Company. The tablets had been crushed and passed through an 8×14 mesh sieve. These catalysts are normally calcined before sale at a temperature of from about 900° F. to about 1100° F. This previously calcined material was then heated to a temperature of 1400° F. for one hour in a muffle furnace. Time and temperature can be modified to bring about changes in alumina physical properties. The presence of steam during this calcining period shortens the time and/or the temperature required for the alumina modification.

The modified improved alumina catalyst obtained had a surface area of about 142 square meters per gram ($M^2/g$) and accumulative pore volume of 0.42 cubic centimeters per gram (cc/g). In addition the catalyst had a pore volume distribution as shown in Table 1 below, as determined using the mercury penetration method utilizing pressures of up to 50,000 psig. The tests were performed on a mercury porisometer, Model 905-1, manufactured by the Micromeritics Corporation of Norcross, Georgia, U.S.A.

TABLE 1

PORE VOLUME DISTRIBUTION

| Pore Diameter (A) | Cumulative Pore Volume cc/g | |
|---|---|---|
| 0–50 | 0.00 | (0.20) |
| 0–65 | 0.04 | (0.38) |
| 0–80 | 0.17 | (0.38) |
| 0–100 | 0.30 | (0.39) |
| 0–250 | 0.33 | (0.39) |
| 0–500 | 0.34 | (0.40) |
| 0–1,000 | 0.35 | (0.40) |
| 0–10,000 | 0.42 | (0.42) |

Comparisons were made using the same alumina prior to the additional calcining treatment, the pore volume distribution for this original alumina shown in parenthesis. Simple subtraction between any two ranges allows determination of the pore volumes in the higher range. Thus, the alumina catalyst useful in the instant invention has a pore volume increase of 0.26 in the 65A° to 100A° range, as compared to the 0.01 increase for the same range using the prior art catalyst.

The process of the instant invention as well as the improvements obtained thereby are more concretely demonstrated with reference to the examples below, wherein all parts and percentages are by weight unless otherwise specified. The examples are intended to exemplify the instant invention and not to limit it.

EXAMPLE 1

The results of methylating 2,6-xylenol in vapor phase using a 0.5 mole ratio of methanol in a continuous reactor (LHSV) and a reactor temperature of 370° C. is shown in Table 2. The reactor was a ½ inch diameter 316 stainless steel tube with a catalyst volume of 15 cubic centimeters (cc). A comparison of runs with a catalyst calcined at the higher temperatures of the instant invention (designated A) vs a standard catalyst (designated B) is shown in the Table. A large difference in selectivity, yield and catalyst life is revealed between the two catalysts. It will be apparent that although the test was conducted with 2,6-xylenol, ortho cresol as well as other xylenols could be substituted for 2,6-xylenol. Phenol can also be methylated.

Table 2

| | VAPOR PHASE 2,6-XYLENOL METHYLATION | | | | | | | | | | | | |
|---|---|---|---|---|---|---|---|---|---|---|---|---|---|
| Hours on Stream | 2 | | 4 | | 6 | | 26 | | 28 | | 47 | 30.5 | 72 |
| Catalyst (A, B) | A | B | A | B | A | B | A | B | A | B | A | B | A |
| MeOH | 0.0 | 0.0 | 0.15 | 0.06 | 0.20 | 0.10 | 0.33 | 0.43 | 0.34 | 0.66 | 0.49 | 0.99 | .95 |
| Phenol | — | 0.56 | — | 0.82 | — | — | — | — | — | — | — | — | — |
| o-Cresol | 2.38 | 5.72 | 2.20 | 3.53 | 1.51 | 3.18 | 1.52 | 0.79 | 0.92 | 0.94 | 1.35 | 1.15 | 0.54 |
| m,p-Cresol | — | 0.65 | — | 0.51 | — | 0.06 | — | — | — | — | — | — | — |
| 2,6-DMA | — | — | 1.52 | Tr | 0.06 | — | — | — | 0.91 | 0.57 | 1.17 | 0.92 | 1.88 |
| 2,6-Xylenol | 63.90 | 50.37 | 63.58 | 59.65 | 63.71 | 59.75 | 68.28 | 67.37 | 69.27 | 67.48 | 70.16 | 70.09 | 76.78 |
| 2,4/2,5-Xylenol | 1.68 | 6.79 | 1.14 | 2.60 | 1.04 | 2.27 | 0.76 | 1.23 | 0.70 | 1.28 | 0.64 | 0.96 | 0.78 |
| 2,3/3,5-Xylenol | 0.40 | 1.80 | 0.27 | 0.45 | 0.27 | 0.41 | 0.16 | 0.23 | 0.10 | 0.20 | 0.15 | 0.20 | 0.16 |
| 3,4-Xylenol | Tr | 0.29 | Tr | Tr | Tr | Tr | Tr | Tr | Tr | Tr | Tr | Tr | Tr |
| 2,4,6-TMP | 7.40 | 10.09 | 6.32 | 8.06 | 6.60 | 8.26 | 4.79 | 5.13 | 4.16 | 4.66 | 3.62 | 4.10 | 2.43 |
| 2,3,6-TMP | 12.28 | 10.46 | 12.63 | 10.65 | 13.11 | 11.69 | 12.72 | 12.82 | 12.37 | 12.47 | 11.64 | 11.56 | 9.71 |
| 2,3,5/2,4,5-TMP | 1.00 | 4.47 | 0.90 | 2.46 | 0.87 | 2.11 | 0.37 | 0.55 | 0.45 | 0.48 | 0.27 | 0.42 | 0.18 |
| 2,3,4/3,4,5-TMP | 0.19 | 0.69 | 0.21 | 0.41 | 0.23 | 0.37 | 0.09 | 0.16 | 0.15 | 0.08 | 0.10 | 0.12 | 0.15 |
| PMB | Tr | 0.40 | Tr | 0.20 | Tr | 0.15 | Tr | Tr | Tr | Tr | Tr | Tr | Tr |
| 2,3,4,6/2,3,5,6-Temp | 5.88 | 5.87 | 6.16 | 6.23 | 6.59 | 6.74 | 5.67 | 5.81 | 5.47 | 5.73 | 4.97 | 5.02 | 3.51 |
| 2,3,4,5-Temp | 0.81 | 0.82 | 0.76 | 1.22 | 0.79 | 1.16 | 0.40 | 0.53 | 0.31 | 0.46 | 0.29 | 0.40 | 0.16 |
| HMB | 0.48 | 0.21 | 0.58 | 0.34 | 0.63 | 0.38 | 0.37 | 0.40 | 0.42 | 0.36 | 0.39 | 0.21 | |
| PMP | 3.30 | 0.77 | 3.76 | 2.81 | 4.33 | 3.46 | 4.87 | 5.00 | 4.77 | 5.19 | 5.22 | 4.66 | 3.38 |
| Selectivity to 2,3,6-TMP | 35.2 | 24.1 | 37.6 | 28.9 | 37.7 | 31.5 | 42.1 | 40.3 | 41.5 | 39.5 | 40.9 | 40.2 | 42.8 |

The major advantages of increased catalyst life, lower isomerization and disproportionation and higher ortho methylation activity and 2,3,6-trimethylphenol production are greatest in the vapor phase reaction. The catalsyt works well in liquid phase 2,6-xylenol methylation being equally or more active in this service than the normal catalyst but selectivity being similar.

EXAMPLE 2

A commercial vapor phase plant catalyst was compared with the catalyst of the instant invention in a vapor phase reaction using a 2-inch diameter salt bath reactor with a feedstock of 50% phenol and 50% xylenol mixture (in weight percents, o cresol 1.19; m,p cresols 4.31; 2,6 xylenol 72.94; 2,4/2,5 xylenols 13.23; 2,3 xylenol 3.44; 2,4,6 trimethylphenol 4.23; and 2,3,6 trimethylphenol 0.96) and a methanol mole ratio of 0.5. The catalyst of the instant invention was compared to the regular plant catalyst (CATAPAL SB, manufactured and sold by Continental Oil Company) which had been further calcined for 1 hour at 1400° F. A comparison of the two catalysts is shown in Table 3. The larger pore catalyst, obtained as a result of the additional calcining, exhibited higher reaction temperatures, indicating much less deactivation. The yield of 2,3,6-trimethylphenol was about 10% higher and isomerization and disproportionation were reduced. The amounts of pentamethylbenzene (0.04%) and 3,4-xylenol (0.02%) for the composite sample of the 72 hour run with the modified catalyst are exceptionally low. These materials are particularly undesirable impurities in 2,3,6-trimethylphenol production. In addition, catalyst lifetime between regenerations is increased, particularly as the xylenol content of the feed is increased.

The data shown in Table 3 was produced using a 325° salt bath at a liquid hourly space velocity (LHSV) of 3.0. The feeds used are indicated in the Table. In Table 3 catalyst A is the catalyst prepared according to the instant invention (CATAPAL SB catalyst further calcined for 1 hour at 1400° F.). Catalyst B is a commercial CATAPAL SB 3/16 inch diameter pellet catalyst normally used in commercial plants originally calcined at about 900° F.

1100° F., and 1500° F., while FIG. 3 shows this effect for temperatures of 1000° F., 1200° F., and 1800° F. These figures indicate that calcining temperatures of 1200° to 1500° F. are preferred, but the temperatures up to 1800° F. can be used.

These tests also showed less pentamethylbenzene (PMB) and 3,4 xylenol by-products produced (0.04% by weight and 0.02% by weight respectively) than usual (0.2% by weight for each) when a feed of 50%/50% xylenol/phenol and a 0.50 methanol mole ratio was used. These materials are highly objectionable impurities because they are not easily separable by distillation from 2,3,6-TMP or the oxidation product of 2,3,6-TMP (2,3,5-trimethylquinone) which is a chemical intermediate in Vitamin E synthesis.

EXAMPLE 3

A phenol methylation was carried out in liquid phase in a continuous reactor (¼ inch stainless steel), using a 0.7 mole ratio of methanol, an LSHV of 6.0 and 650 psig. A temperature of 400° C. was used. The catalyst was CATAPAL SB, described above, calcined for an additional 1 hour at 1400° F. and passed through a 10 × 16 mesh. The results obtained show low m,p cresol formation.

| | |
|---|---|
| DME | 0.30 |
| MeOH | 0.09 |
| anisole | 1.48 |
| phenol | 46.15 |
| o-me anisole | 0.31 |
| o-cresol | 34.41 |
| m,p-cresol | 0.22 |
| 2,6-xylenol | 11.18 |
| 2,4/2,5-xylenol | 1.66 |
| 2,3,-xylenol | 0.89 |
| 2,4,6-TMP | 0.46 |
| 2,3,6-TMP | 1.95 |
| 2,3,5/2,4,5-TMP | 0.22 |
| 2,3,4/3,4,5-TMP | 0.10 |
| 2,3,4,6/2,3,5,6-TMP | 0.61 |
| 2,3,4,5 | 0.06 |
| PMP | 0.30 |
| | 100.0 |

TABLE 3
COMPARISON OF REGULAR AND MODIFIED PLANT CATALYST

| Product period, Hrs. | Feed | 0–4 | | 4–8 | | 8–24 | | 24–48 | | 48–72 | | (55) | | | | Composite | |
|---|---|---|---|---|---|---|---|---|---|---|---|---|---|---|---|---|---|
| Cumulative Hours | | 4 | | 8 | | 24 | | 48 | | 72 | | 55 | | 72 | 55 | 72 | 55 |
| Catalyst (A,B) | | A | B | A | B | A | B | A | B | A | B | A | B | A | B | A | B |
| DME | | 0.04 | 0.13 | 0.05 | 0.08 | 0.08 | 0.16 | 0.19 | 0.27 | 0.25 | 0.32 | 0.25 | 0.37 | 0.17 | 0.22 |
| MeOH | 13.09 | 0.03 | 0.05 | 0.16 | 0.09 | 0.13 | 0.24 | 0.20 | 0.22 | 0.35 | 0.54 | 0.38 | 0.92 | 0.23 | 0.42 |
| Anisole | | 0.05 | 0.06 | 0.10 | 0.09 | 0.13 | 0.18 | 0.24 | 0.45 | 0.31 | 0.58 | 0.35 | 0.51 | 0.22 | 0.38 |
| Phenol | 50.34 | 22.48 | 24.32 | 24.32 | 23.27 | 25.41 | 25.26 | 26.60 | 26.80 | 27.38 | 27.80 | 27.36 | 28.23 | 26.21 | 26.15 |
| o-Me-anisole | | — | — | — | — | — | 0.03 | — | 0.06 | — | 0.06 | 0.06 | 0.06 | 0.04 | 0.05 |
| o-Cresol | 0.59 | 20.81 | 19.41 | 18.69 | 19.46 | 17.87 | 17.79 | 16.77 | 16.85 | 16.75 | 16.03 | 16.28 | 15.85 | 16.92 | 17.13 |
| m,p-Cresol | 2.14 | 4.34 | 4.96 | 3.27 | 3.61 | 2.57 | 2.71 | 1.54 | 1.57 | 1.31 | 1.43 | 1.29 | 1.45 | 2.31 | 2.55 |
| 2,6-DMA | | — | — | — | — | — | — | — | — | — | Tr | Tr | Tr | Tr | Tr |
| 2,6-Xylenol | 36.22 | 27.32 | 26.71 | 30.31 | 30.73 | 32.20 | 33.63 | 33.91 | 35.93 | 34.72 | 36.81 | 34.74 | 37.00 | 33.19 | 34.40 |
| 2,4/2,5 Xylenol | 6.57 | 8.99 | 9.38 | 7.99 | 8.08 | 7.18 | 7.02 | 6.57 | 6.22 | 6.24 | 5.82 | 6.27 | 5.78 | 6.86 | 6.76 |
| 2,3/3,5-Xylenol | 1.56 | 2.73 | 2.95 | 2.21 | 2.18 | 1.78 | 1.72 | 1.58 | 1.43 | 1.18 | 1.01 | 1.42 | 1.02 | 1.65 | 1.60 |
| 2,4-Xylenol | | 0.58 | 0.71 | 0.36 | 0.42 | 0.21 | 0.22 | 0.13 | Tr | Tr | Tr | Tr | Tr | 0.17 | 0.21 |
| 2,4,6-TMP | 2.10 | 2.68 | 2.64 | 2.80 | 2.30 | 2.80 | 2.26 | 2.92 | 2.10 | 2.65 | 1.90 | 2.97 | 1.89 | 2.85 | 2.18 |
| 2,3,6-TMP | 0.47 | 4.01 | 3.75 | 4.25 | 3.90 | 4.49 | 4.10 | 4.62 | 4.14 | 4.57 | 4.11 | 4.60 | 4.09 | 4.52 | 4.07 |
| 2,3,5/2,4,5-TMP | | 2.24 | 2.58 | 1.71 | 1.85 | 1.26 | 1.33 | 0.95 | 0.87 | 0.75 | 0.70 | 0.71 | 0.67 | 1.06 | 1.16 |
| 2,3,4/3,4,5-TMP | | 0.62 | 0.71 | 0.62 | 0.37 | 0.44 | 0.42 | 0.54 | 0.37 | 0.40 | 0.35 | 0.39 | 0.31 | 0.44 | 0.26 |
| PMB | | 0.22 | 0.30 | 0.05 | 0.12 | Tr | 0.10 | Tr | Tr | Tr | Tr | Tr | Tr | Tr | Tr |
| 2,3,4,6/2,3,5,6-TeMP | | 1.76 | 1.74 | 1.83 | 1.70 | 1.86 | 1.72 | 1.83 | 1.64 | 1.85 | 1.80 | 1.78 | 1.57 | 1.85 | 1.65 |
| 2,3,4,5/2,3,5,6-TeMP | | 0.37 | 0.41 | 0.39 | 0.40 | 0.39 | 0.38 | 0.35 | 0.32 | 0.33 | 0.28 | 0.31 | 0.35 | 0.36 | 0.34 |
| HMB | | Tr | Tr | Tr | — | Tr | 0.03 | Tr | Tr | Tr | Tr | Tr | Tr | Tr | Tr |
| PMB | | 0.80 | 0.72 | 1.06 | 0.89 | 1.27 | 1.13 | 1.42 | 1.23 | 1.50 | 1.31 | 1.48 | 1.21 | 1.35 | 1.13 |

In addition, a comparison of the life of the two catalysts is shown in FIG. 1. FIG. 1 clearly shows that one outstanding feature of the instant catalyst is the temperature in the reaction as a function of time. Here the larger pore catalyst exhibits higher temperature indicating much less deactivation.

FIGS. 2 and 3 show the effect of calcining temperature of alumina extrudate pore size distribution. FIG. 2 shows the effect for calcining temperatures of 900° F., Average pore diameters have been calculated using an empirical formula, ($CPV/S$ = average pore size, where $PV$ = cumulative pore volume, $S$ = surface area and $C$ is constant), as set forth in *Introduction to Principles of Heterogenous Catalysis*, Chapter 4, Thomas and Thomas, Academic Press, N.Y. (1967). Pore volume distribution for 1400° F. calcining is shown. When the same feedstock was compared using 24 hour activity tests and a small laboratory reactor to determine the optimum range of surface area and average pore diameter, it became apparent that pore diameter has a marked affect upon catalyst performance, which is tempered by the surface area. The effects of heat treatment are shown in Table 4, the alumina tested being the same as described above.

TABLE 4
EFFECTS OF HEAT TREATMENT

| Temperature °F | Time at Maximum Temperature | Surface Area m²/g | Estimated Average Pore Diameter, A |
|---|---|---|---|
| 1000 | 3 | 200 | 50 |
| 1200 | 1 | 172 | 65 |
| 1400 | 1 | 142 | 80 |
| 1600 | 1 | 114 | 95 |
| 1800 | 1 | 72 | 150 |

Table 5 shows the vapor phase methylation of a phenol/mixed cresylic feed using methanol and catalysts calcined at varying temperatures. In the table, all catalysts were prepared to an 8×14 mesh, with A being a control CATAPAL SB alumina, B-additional 1 hour heating at 1200° F., C-additional 1 hour at 1400° F., D-additional 1 hour at 1600° F., and E-additional 1 hour at 1800° F., all individually compared to A. The reaction was carried out in an electrically heated reactor in a continuous fashion with an LHSV of 3. A comparison of the results show extremely good results for the C and D catalysts in 2,3,6-trimethylphenol and 2,6 xylenol desired products with a corresponding decrease in by-products.

TABLE 5
VAPOR PHASE METHYLATION OVER VARYING SURFACE AREA & PORE DIAMETER CATAPAL® ALUMINA

| Hours | | 0–4 | | | | | 4–7 | | | |
|---|---|---|---|---|---|---|---|---|---|---|
| Catalyst | Feed | A | B | C | D | E | A | B | C | D | E |
| DME | — | 0.03 | — | 0.02 | 0.09 | 0.12 | 0.04 | Tr | 0.07 | 0.09 | 0.17 |
| MeOH | 13.09 | — | — | 0.20 | 0.12 | Tr | — | — | 0.20 | 0.04 | Tr |
| Anisole | — | — | — | 0.17 | 0.25 | — | — | — | 0.15 | 0.09 | 0.28 |
| Phenol | 50.34 | 20.82 | 23.22 | 25.39 | 25.21 | 24.01 | 22.79 | 24.69 | 25.70 | 25.29 | 24.18 |
| o-Me Anisole | — | — | — | — | 0.04 | — | — | — | — | — | 0.05 |
| o-Cresol | 0.59 | 23.38 | 20.89 | 19.30 | 18.95 | 20.64 | 21.25 | 19.28 | 18.56 | 18.62 | 19.97 |
| m,p-Cresol | 2.14 | 4.24 | 2.65 | 1.33 | 1.13 | 1.48 | 2.88 | 1.43 | 1.29 | 1.20 | 1.30 |
| 2,6-Xylenol | 36.22 | 28.65 | 32.98 | 35.17 | 36.53 | 35.40 | 32.62 | 35.23 | 36.11 | 36.86 | 35.84 |
| 2,4/2,5-Xylenol | 6.57 | 8.82 | 6.92 | 6.22 | 5.67 | 6.27 | 7.29 | 6.08 | 5.86 | 5.63 | 5.98 |
| 2,3/3,5-Xylenol | 1.56 | 2.70 | 1.83 | 1.57 | 1.33 | 1.53 | 1.91 | 1.55 | 1.40 | 1.30 | 1.51 |
| 3,4-Xylenol | | 0.58 | 0.27 | Tr | Tr | 0.10 | 0.28 | 0.03 | Tr | Tr | Tr |
| 2,4,6-TMP | 2.10 | 2.23 | 2.10 | 2.00 | 1.99 | 2.09 | 2.21 | 2.14 | 1.98 | 2.01 | 2.11 |
| 2,3,6-TMP | 0.47 | 3.56 | 4.21 | 4.28 | 4.62 | 4.35 | 4.02 | 4.67 | 4.47 | 4.76 | 4.52 |
| 2,3,5/2,4,5-TMP | | 2.30 | 1.53 | 1.13 | 0.82 | 1.08 | 1.60 | 1.03 | 0.90 | 0.74 | 0.94 |
| 2,3,4/3,4,5-TMP | | 0.51 | 0.41 | 0.34 | 0.33 | 0.34 | 0.43 | 0.37 | 0.32 | 0.26 | 0.37 |
| PMB | | 0.21 | 0.16 | 0.11 | 0.04 | 0.05 | 0.16 | 0.14 | 0.08 | Tr | 0.05 |
| 2,3,4,6/2,3,5,6-TeMP | | 1.38 | 1.68 | 7.68 | 1.68 | 1.59 | 1.61 | 1.81 | 1.69 | 1.71 | 1.63 |
| 2,3,4,5-TeMP | | 0.32 | 0.45 | 0.43 | 0.35 | 0.36 | 0.42 | 0.46 | 0.43 | 0.35 | 0.35 |
| PMP | | 0.28 | 0.67 | 0.88 | 1.06 | 0.76 | 0.53 | 1.08 | 1.06 | 1.06 | 0.88 |
| 2,6-DMA | | — | — | — | — | Tr | — | — | — | — | Tr |
| HMB | | Tr | Tr | Tr | Tr | — | Tr | Tr | Tr | Tr | Tr |

| Hours | 7–23 | | | | | 23–24 | | | | |
|---|---|---|---|---|---|---|---|---|---|---|
| Catalyst | A | B | C | D | E | A | B | C | D | E |
| DME | 0.08 | 0.09 | 0.07 | 0.15 | 0.25 | 0.13 | 0.12 | 0.12 | 0.21 | — |
| MeOH | 0.06 | Tr | 0.12 | 0.23 | 0.18 | 0.07 | 0.05 | 0.08 | 0.17 | — |
| Anisole | 0.12 | 0.10 | 0.13 | 0.35 | 0.61 | 0.23 | 0.14 | 0.25 | 0.45 | — |
| Phenol | 24.08 | 25.45 | 25.90 | 26.40 | 25.23 | 24.22 | 26.00 | 26.47 | 26.96 | — |
| o-Me Anisole | — | — | — | 0.05 | 0.07 | — | — | 0.03 | 0.05 | — |
| o-Cresol | 20.29 | 18.45 | 18.02 | 17.96 | 20.20 | 19.30 | 18.25 | 17.50 | 17.31 | — |
| m,p-Cresol | 1.49 | 1.26 | 1.25 | 1.10 | 1.19 | 1.48 | 1.15 | 1.11 | 1.00 | — |
| 2,6-Xylenol | 34.41 | 36.33 | 37.16 | 36.85 | 36.05 | 35.76 | 36.90 | 37.52 | 37.42 | — |
| 2,4/2,5-Xylenol | 6.64 | 5.77 | 5.52 | 5.43 | 5.78 | 6.34 | 5.52 | 5.34 | 5.33 | — |
| 2,3/3,5-Xylenol | 1.60 | 1.35 | 1.03 | 1.00 | 1.13 | 1.45 | 1.01 | 0.95 | 0.95 | — |
| 3,4-Xylenol | 0.19 | Tr | Tr | Tr | Tr | 0.10 | Tr | Tr | Tr | — |
| 2,4,6-TMP | 2.18 | 2.11 | 1.87 | 1.94 | 1.83 | 2.27 | 1.97 | 1.84 | 1.89 | — |
| 2,3,6-TMP | 4.28 | 4.72 | 4.76 | 4.71 | 4.23 | 4.40 | 4.68 | 4.70 | 4.60 | — |
| 2,3,5/2,4,5-TMP | 1.25 | 0.79 | 0.71 | 0.64 | 0.84 | 1.01 | 0.69 | 0.61 | 0.56 | — |
| 2,3,4/3,4,5-TMP | 0.40 | 0.20 | 0.20 | 0.26 | 0.26 | 0.27 | 0.20 | 0.24 | 0.26 | — |
| PMB | 0.15 | 0.07 | Tr | Tr | Tr | 0.05 | 0.06 | Tr | Tr | — |
| 2,3,4,6/2,3,5,6-TeMP | 1.68 | 1.77 | 1.77 | 1.72 | 1.48 | 1.67 | 1.73 | 1.71 | 1.65 | — |
| 2,3,4,5-TeMP | 0.42 | 0.40 | 0.39 | 0.33 | 0.31 | 0.44 | 0.39 | 0.35 | 0.30 | — |
| PMP | 0.81 | 1.27 | 1.30 | 1.25 | 0.78 | 1.01 | 1.31 | 1.36 | 1.29 | — |
| 2,6-DMA | — | — | — | — | Tr | — | — | — | — | — |
| HMB | Tr | Tr | Tr | Tr | — | Tr | Tr | Tr | Tr | — |

The data comparisons clearly show that the modified alumina catalyst of the instant invention allows highly improved vapor phase methylation of phenol, xylenols, and 2,3,6-trimethylphenol. Selectivities and catalyst life are greatly improved, thus allowing retention of the advantages of carrying out a vapor phase reaction while obtaining many of the benefits of a liquid phase reaction.

I claim:

1. In the process for the vapor phase methylation of phenol, cresols, and xylenols using methanol at temperatures of from about 300° C. to about 450° C. and pressures of from about 0.01 to about 100 pounds per square inch gauge in the presence of an alumina or alumina-based catalyst derived from the hydrolysis of aluminum alkoxides, the improvement comprising calcining the alumina, prior to use as a methylation catalyst, at temperatures of from about 1150° F. to about 1800° F. for from about 0.5 to about 12 hours to produce an alumina having at least 50% of the pores larger than about 65 angstroms and at least 50% of the pores smaller than about 200 angstroms, then carrying out the reaction in a continuous reactor at a liquid hourly space velocity (LHSV) of from 2 to 10.

2. The method as described in claim 1 wherein the starting material is phenol, the methylating agent is methanol, the temperature is from about 300° C. to about 450° C., the mole ratio of methanol is from about 0.3 to 1.0, the LHSV is from about 2 to about 10, the pressure is from about 1 to about 100 psig, and the reaction is carried out in vapor phase to produce predominantly o-cresol, 2,6-xylenol and 2,3,6-trimethylphenol.

* * * * *

UNITED STATES PATENT OFFICE
CERTIFICATE OF CORRECTION

PATENT NO. : 4,126,749
DATED : November 21, 1978
INVENTOR(S) : Bruce E. Leach

It is certified that error appears in the above-identified patent and that said Letters Patent are hereby corrected as shown below:

Column 9, line 10, "0.01" should be --0.1--.

Table 5, under 0-4, Column C, (same line as 2,3,4,6/2,3,5,6-TeMP in Column 1), "7.68" should be --1.68--.

Signed and Sealed this

Eleventh Day of March 1980

[SEAL]

Attest:

SIDNEY A. DIAMOND

Attesting Officer

Commissioner of Patents and Trademarks